United States Patent [19]

Tavares et al.

[11] 3,996,290
[45] Dec. 7, 1976

[54] 2,4-DIMETHYL-2-PHENYL-4-PENTENAL

[75] Inventors: Robert F. Tavares, Cedar Grove; Jack Agran, Wallington, both of N.J.

[73] Assignee: Givaudan Corporation, Clifton, N.J.

[22] Filed: June 11, 1975

[21] Appl. No.: 585,935

[52] U.S. Cl. .............................. 260/599; 252/522
[51] Int. Cl.$^2$ ........................................ C07C 47/52
[58] Field of Search .................................... 260/599

[56] References Cited
UNITED STATES PATENTS

| | | | |
|---|---|---|---|
| 3,023,247 | 2/1962 | Scriabine | 260/599 |
| 3,793,376 | 2/1974 | Hall et al. | 260/599 |
| 3,862,235 | 1/1975 | Himmele | 260/599 X |
| 3,862,340 | 1/1975 | Schreiber | 260/599 X |
| 3,879,425 | 4/1975 | Hall et al. | 260/599 X |

*Primary Examiner*—Bernard Helfin
*Attorney, Agent, or Firm*—Thomas Cifelli, Jr.

[57] ABSTRACT

2,4-Dimethyl-2-phenyl-4-pentenal possesses a strong rose geranium type odor which is especially valuable in perfumery. Compounds of closely related structure do not possess this quality.

1 Claim, No Drawings

2,4-DIMETHYL-2-PHENYL-4-PENTENAL

BACKGROUND OF THE INVENTION

1. Field of the Invention
A novel odorant aldehyde.
2. Prior Art
2,4-Dimethyl-2-phenyl-4-pentenal has not been described in the prior art.

SUMMARY OF THE INVENTION

The compound of the present invention has the following structure:

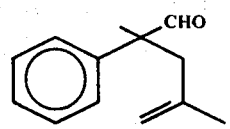

In accordance with the preferred process of the present invention, hydratropic aldehyde is reacted with methallyl chloride. The reaction may be illustrated as follows:

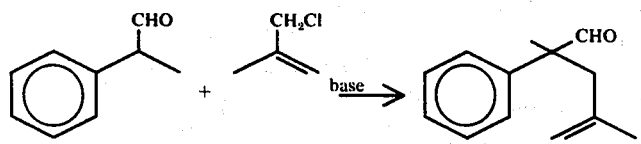

The compound of the present invention has a strong rose geranium type odor. The compound is useful as an odorant and may be used in perfumes, soaps and other toilet goods.

DESCRIPTION OF THE PREFERRED EMBODIMENTS

The aldehyde of the present invention, 2,4-dimethyl-2-phenyl-4-pentenal, can be prepared by the base catalyzed alkylation of hydratropic aldehyde (2-phenylpropanal) with methallyl chloride (2-methyl-2-propenyl chloride) in accordance with the following equation:

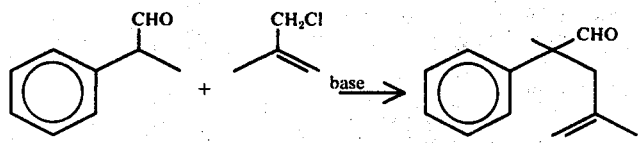

While the economical methallyl chloride is preferred, it is understood that the bromide or iodide are not as preferred because of greater expense. Any analogous compound in which the chlorine was replaced by a suitable leaving group would be applicable.

In preparing the novel aldehyde, it is preferred to react an excess of the more economical methallyl chloride since dialkylation is not a problem. However, the relative quantities of the reagents are not critical to this invention.

The alkylation of this invention is effected by adding to the reaction medium a sufficient amount of base which is sufficiently strong enough to activate the hydratropic aldehyde. It is generally accepted by those practiced in the art that such alkylations proceed by forming a carbanion α to the activating group which then reacts with an organic halide to form the alkylated product and a halide salt. It is also generally accepted that the base required may be dependent upon the reaction conditions used such as temperature and solvent. We prefer to use sodium methoxide as base and methanol as solvent for reasons of economy, however, it is recognized that other conditions known in the art for the alkylation of carbanions may also be applicable. Other common bases that may be used are metal alkoxides (sodium ethoxide, potassium), metal alkyls, metal hydrides (sodium hydride etc.) and the like. Solvents such as alcohols, tetrahydrofuran, dimethyl sulfoxide, dimethyl formamide, toluene and the like are also suitable.

Suitable temperatures can range from below 0° to above 100° C depending on the reaction apparatus (closed or open system), solvent and base used. It is preferred to conduct the reaction between 20° C (room temperature) and 72° C (boiling point of methallyl chloride).

The preferred method provides, surprisingly, a good yield of product (84%). Most of the examples in the literature involve the alkylation of carbons α to ketones, nitriles etc. whereas there is a dearth of examples of alkylation of carbons α to aldehydes. This is due to the propensity of aldehydes to enter into side reactions such as self-condensation. It is therefore surprising that the process of this invention provides the 2,4-dimethyl-2-phenyl-4-pentenal in such high yield and that the reaction provides a product essentially free of undesirable by-products.

Although other sequences of addition will provide the desired product, it is preferred to add the base to the reactants, such a sequence having been found to provide the desired product in good yield. In the preferred process, the reactants are dissolved in a suitable solvent and the base added at a rate sufficient to keep the temperature rise due to the heat of reaction under control.

It is particularly surprising that compounds of closely related structure do not possess the fine geranium rose odor of the 2,4-dimethyl-2-phenyl-4-pentenal. Table I below compares the odors of the novel aldehyde, 2,4-dimethyl-2-phenyl-4-pentenal with homologs and other compounds of similar structure.

TABLE I

| Compound | Odor |
|---|---|
| 2,4-dimethyl-2-phenyl-4-pentenal | rose, geranium |
| 2-methyl-2-p-tolyl-4-pentenal | hay, acetophenone |
| 2-methyl-2-phenyl-4-pentenal | harsh, grape |
| 2,5-dimethyl-2-phenyl-4-hexenal | floral, aceto- |

TABLE I-continued

| Compound | Odor |
| --- | --- |
| 2,4-dimethyl-2-p-tolyl-4-pentenal | phenone, rose fruity, hay, acetophenone |

Only the 2,4-dimethyl-2-phenyl-4-pentenal was found to have the desirable rose-geranium note and was the only compound of Table I considered by the perfumers as having any value as an odorant for perfume compositions.

The 2,4-dimethyl-2-phenyl-4-pentenal is particularly valuable in perfumery because of its fresh floral nuances and its intensity enhancing properties. It is most useful in providing the natural green and floral nuances in rose or geranium type formulations. The compound can be used in most perfumes and fragrances in the ratio of about 1 to 200 parts per thousand of odorant compositions containing the compound. Larger quantities of the 2,4-dimethyl-2-phenyl-4-pentenal, e.g., 20–90 percent by weight of the odorant formulation can be used to achieve special effects.

The odorant compositions containing the compound of this invention can be used as odorant bases for the preparation of perfumes and toilet waters by adding the usual alcoholic and aqueous diluents thereto; approximately 15–20% by weight of base would be used for the former and approximately 3–5% by weight would be used for the latter.

Similarly, the base compositions can be used to odorize soaps, detergents, cosmetics, or the like. In these instances a base concentration of from about 0.5 to about 2% by weight can be used.

The following Examples are provided to illustrate further the practice of the present invention, but are for purposes of preferred embodiments only and should not be construed as limiting.

EXAMPLE I

Preparation of 2,4-Dimethyl-2-phenyl-4-pentenal

To a three liter flask equipped with a thermometer, agitator, a Greiner-Friedrichs distilling condenser for removing solvents and a feed funnel for solids was charged 339 g of recently distilled methallyl chloride (2-methyl-2-propenyl chloride) and 600 g of dry methaol. Sufficient sodium methylate (about one gram dry powder) was added to make the reaction mixture alkaline to phenolphthalein.

The hydratropic aldehyde was then added over a 5 minute period followed immediately by the slow addition of dry sodium methylate. Heat of reaction caused the temperature to rise to 50° C. The sodium methylate was added over a period of twenty-five minutes during which time the temperature was maintained between 45° C and 50° C by cooling with an ice water bath when necessary. The batch was then stirred for 1 hour. The temperature was maintained below 50° C with an ice water bath at the beginning of the hour and then dropped slowly to 40° C at the end of the hour.

The batch was then cooled to room temperature and enough glacial acetic acid (40 grams) was added to make the reaction mixture acidic enough to turn blue litmus paper to red. The methanol was then removed atmospherically until the temperature in the reaction vessel reached 85° C.

The reaction mixture was cooled 50° C. Water (900 g) and toluene (525 g) were added and the batch was agitated until the salts dissolved (5 minutes). The organic layer was washed with water, then 5% sodium carbonate, and then water (each wash being about 300 ml). The reaction mixture was then distilled to remove the toluene and the oil vacuum distilled to remove the toluene and the oil vacuum distilled to obtain 339 grams (84% of theoretical) of 2,4-dimethyl-2-phenyl-4-pentenal having a boiling point of 86° C at a pressure of 1.0 millimeters of mercury (refractive index, $n_D^{20}$ – 1.5250). The mass spectrometer showed a molecular ion at m/e 188.

EXAMPLE II

Use of 2,4-dimethyl-2-phenyl-4-pentenal as an odorant

A Rose de Mai type perfume was formulated with the 2,4-dimethyl-4-pentenal prepared as in the Example I. The composition of the perfume formulation is provided in Table II below.

TABLE II

ROSE PERFUME

| Ingredient | Parts by weight |
| --- | --- |
| Phenyl ethyl alcohol | 300 |
| Geraniol | 300 |
| Citronellol | 50 |
| Trichloromethylphenylcarbinyl acetate | 100 |
| Aldehyde C-9 (10% solution in ethanol) | 5 |
| Aldehyde C-11 undecylenic (10% solution in ethanol) | 20 |
| Geranyl acetate | 20 |
| Methyl heptine carbonate | 5 |
| Benzyl benzoate | 195 |
| 2,4-Dimethyl-2-phenyl-4-pentenal | 5 |
| | 1000 |

The addition of 2,4-dimethyl-2-phenyl-4-pentenal at a concentration of ½ % by weight intensifies the blend of the rose perfume imparting to it a natural green character reminiscent of the oxides in natural rose oil. The perfume without the 2,4-dimethyl-2-phenyl-4-pentenal lacks this natural green character and is not as desirable to the perfumer.

For purposes of contrast, several aldehydes having structures closely related to the 2,4-dimethyl-2-phenyl-4-pentenal were prepared by methods similar to that described in Example I. The aldehydes prepared in this manner are listed in Table I presented earlier.

None of the aldehydes listed in Table I exhibited any odorant properties useful in perfumery. When it was attempted to prepare a perfume composition of the type illustrated in Example II above by substituting each of the aldehydes of Table I for the 2,4-dimethyl-2-phenyl-4-pentenal, no improvement in the perfume odor was obtained and, in fact, in most cases a detrimental effect was observed.

What is claimed is:
1. 2,4-Dimethyl-2-phenyl-4-pentenal.

* * * * *